(12) United States Patent
Freitag et al.

(10) Patent No.: US 7,928,259 B2
(45) Date of Patent: *Apr. 19, 2011

(54) DIARYL ALKYLPHOSPHONATES AND METHODS FOR PREPARING SAME

(75) Inventors: Dieter Freitag, Chelmsford, MA (US); Savvas Hadjikyriacou, Chelmsford, MA (US)

(73) Assignee: FRX Polymers, Inc., Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/029,629

(22) Filed: Feb. 12, 2008

(65) Prior Publication Data

US 2009/0203942 A1 Aug. 13, 2009

(51) Int. Cl.
C07F 9/02 (2006.01)
C07F 9/28 (2006.01)

(52) U.S. Cl. .................................................. 558/115

(58) Field of Classification Search .................. None
See application file for complete search history.

(56) References Cited

U.S. PATENT DOCUMENTS

| | | | |
|---|---|---|---|
| 2,534,242 A | 11/1949 | Cusic | |
| 2,682,522 A | 6/1954 | Coover, Jr. et al. | |
| 2,716,101 A | 8/1955 | Coover, Jr. et al. | |
| 3,153,008 A | 10/1964 | Fox | |
| 3,271,329 A | 9/1966 | Coover, Jr. et al. | |
| 3,326,852 A | 6/1967 | Thomas | |
| 3,442,854 A | 5/1969 | Curtius et al. | |
| 3,932,351 A | 1/1976 | King | |
| 3,932,566 A | 1/1976 | Reader | |
| 3,952,072 A | 4/1976 | Yonemitsu et al. | |
| 4,033,927 A | 7/1977 | Borman | |
| 4,048,106 A | 9/1977 | Hermans | |
| 4,064,107 A | 12/1977 | Stackman et al. | |
| 4,078,016 A | 3/1978 | Kramer | |
| 4,093,582 A | 6/1978 | Mark et al. | |
| 4,152,373 A | 5/1979 | Honig | |
| 4,223,104 A | 9/1980 | Kim et al. | |
| 4,254,177 A | 3/1981 | Fulmer | |
| 4,322,520 A | 3/1982 | Schmidt et al. | |
| 4,328,174 A | 5/1982 | Schmidt et al. | |
| 4,331,614 A | 5/1982 | Schmidt et al. | |
| 4,332,921 A | 6/1982 | Schmidt et al. | |
| 4,374,971 A | 2/1983 | Schmidt et al. | |
| 4,377,537 A | 3/1983 | Block et al. | |
| 4,401,802 A | 8/1983 | Schmidt et al. | |
| 4,408,033 A | 10/1983 | Hefner, Jr. | |
| 4,415,719 A | 11/1983 | Schmidt et al. | |
| 4,474,937 A | 10/1984 | Bales | |
| 4,481,350 A | 11/1984 | Schmidt et al. | |
| 4,508,890 A | 4/1985 | Schmidt et al. | |
| 4,594,404 A | 6/1986 | Kawakami et al. | |
| 4,642,366 A | 2/1987 | Honig et al. | |
| 4,719,279 A | 1/1988 | Kauth et al. | |
| 4,736,052 A | 4/1988 | Nunan et al. | |
| 4,762,905 A | 8/1988 | Schmidt et al. | |
| 4,782,123 A | 11/1988 | Kauth et al. | |
| 5,003,029 A | 3/1991 | Ueda et al. | |
| 5,034,056 A | 7/1991 | VonBonin | |
| 5,039,775 A | 8/1991 | Oyaizu | |
| 5,086,153 A | 2/1992 | Oyaizu | |
| 5,216,113 A | 6/1993 | Schulz-Schlitte et al. | |
| 5,319,058 A | 6/1994 | Hattori et al. | |
| 5,334,692 A | 8/1994 | Hess et al. | |
| 5,525,681 A | 6/1996 | Barron et al. | |
| 5,639,800 A | 6/1997 | VonBonin et al. | |
| 5,719,200 A | 2/1998 | Staendeke et al. | |
| 5,919,844 A | 7/1999 | Shimizu et al. | |
| 6,066,700 A | 5/2000 | Konig et al. | |
| 6,291,630 B1 | 9/2001 | Konig et al. | |
| 6,861,499 B2 | 3/2005 | Vinciguerra | |
| 2004/0167284 A1 | 8/2004 | Vinciguerra et al. | |
| 2005/0020800 A1 | 1/2005 | Levchik et al. | |
| 2005/0222370 A1 | 10/2005 | Freitag et al. | |
| 2006/0020104 A1 | 1/2006 | Freitag | |
| 2007/0203355 A1 | 8/2007 | Freitag et al. | |

FOREIGN PATENT DOCUMENTS

| | | |
|---|---|---|
| DE | 2747554 A1 | 4/1979 |
| EP | 0034239 A1 | 8/1981 |
| EP | 0077493 B1 | 3/1987 |
| GB | 2043083 | 1/1980 |
| WO | WO 03/029258 A1 | 4/2003 |
| WO | WO 2004/076536 | 9/2004 |
| WO | WO 2004/076537 | 9/2004 |
| WO | WO 2007/079272 A2 | 7/2007 |

OTHER PUBLICATIONS

Yao et al., {A concise method for synthesis of diaryl aryl- or alkylphosphonates, Tetrahedron Letters (2005), Volume Date 2006, 47(3), 277-281}.*

Yao et al., A concise method for the synthesis of diaryl aryl- or alkylphosphonates, 2005, Tetrahedron Lett. 47(22):277-281.

Schmidt et al., Aromatische Polyphosphonate: Thermoplastische Polymere von extremer Brandwidrigeit, 1985, Die Angewandte Makromolekulare Chemie, 132(2165):1-8.

Billmeyer, Textbook of Polymer Science, $2^{nd}$ ed., Wiley Interscience, New York, 1971, pp. 45-52.

Legrand et al., eds., Handbook of Polycarbonates, Marcel Dekker, Inc., New York, 2000 (TOC).

Cotter et al., Engineering Plastics: A Handbook of Polyarylethers, Science Publ. S.A., Switzerland 1995 (TOC). Groggins, Unit Processes in Organic Synthesis, $4^{th}$ ed., McGraw Hill Book Co., 1952, pp. 616-620.

Morgan, Condensation Polymers, Wiley Interscience, New York, 1965, pp. 217-223.

Levchik et al., Overview of Recent Developments in the Flame Retardancy of Polycarbonates, 2005, Polymer International, 54(7):981-998.

Levchik et al., Overview of Recent Developments in the Flame Retardancy of Polycarbonates, Polymer International, 54(7):981-998.

* cited by examiner

*Primary Examiner* — Daniel M Sullivan
*Assistant Examiner* — Yevegeny Valenrod
(74) *Attorney, Agent, or Firm* — Pepper Hamilton LLP

(57) ABSTRACT

A method for preparing substantially pure optionally substituted diaryl alkylphosphonates from an optionally substituted triarylphosphite and an optionally substituted trialkylphosphite or an optionally substituted alkanol under special reaction conditions is described.

24 Claims, No Drawings

DIARYL ALKYLPHOSPHONATES AND METHODS FOR PREPARING SAME

BACKGROUND

Various methods for the synthesis of diaromatic alkylphosphonates are known. Methods for making diaromatic alkylphosphonates are described in U.S. Pat. Nos. 4,152,373 and 4,377,537, for example. In U.S. Pat. No. 4,152,373, diaromatic alkylphosphonates are prepared by the reaction of a triaromaticphosphite specifically triphenylphosphite and methanol in the presence of a catalytic amount of methyl iodide. The reaction temperatures are higher than the boiling point of methanol (~65° C.), and consequently require a relatively slow addition of methanol in order to keep it from boiling out of the reactor. In this reaction, phenol is a by-product that is distilled from the product in a separate step.

U.S. Pat. No. 4,377,537 describes a method of synthesizing diaromatic methylphosphonates by the reaction of a triarylphosphite (specifically triphenylphosphite) and trialkylphosphite (specifically trimethylphosphite) in the presence of a catalytic amount of methyl iodide. The reaction typically involves heating the components to a final temperature of about 230° C. for up to 1 hour. Exothermic reactions for this process occur in two temperature regions, the first around 100° C., and the second near 210° C. Due to the exothermic (even explosive) nature of these reactions when used in a batch process, the reaction scheme described in U.S. Pat. No. 4,377,537 is limited to small scale production of diaromatic alkylphosphonates.

Although some diaromatic alkylphosphonates (e.g. diphenyl methylphosphonate) (Registry number 7526-26-3) are commercially available, they are relatively expensive.

SUMMARY

Embodiments of the invention presented herein include a method for preparing optionally substituted diaryl alkylphosphonate including the steps of: combining at least one optionally substituted triarylphosphite and at least one catalyst to form a triarylphosphite catalytic mixture; heating the triarylphosphite catalytic mixture to a reaction temperature; adding to the heated triarylphosphite catalytic mixture: (i) at least one optionally substituted trialkylphosphite in a molar excess of less than about 10% based on the optionally substituted triarylphosphite; or (ii) at least one optionally substituted alkanol in a molar excess of less than about 10% based on the optionally substituted triarylphosphite; and reacting the triarylphosphite mixture and the at least one optionally substituted trialkylphosphite or at least one optionally substituted alkanol to form the optionally substituted diaryl alkylphosphonate.

In some embodiments the optionally substituted trialkylphosphite may be in a molar excess of 0.0% to about 3% of the optionally substituted triarylphosphite, and in others, the optionally substituted trialkylphosphite may be in a molar excess of less than about 1% of the optionally substituted triarylphosphite. In particular embodiments, the triarylphosphite catalytic mixture is stored for an indefinite period of time prior to heating.

The optionally substituted triarylphosphite of various embodiments may be of general formula (III):

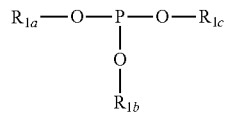

where $R_{1a}$, $R_{1b}$ and $R_{1c}$ my each, independently, be of general formula (II):

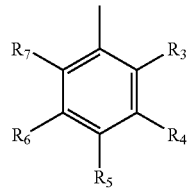

where $R_3$, $R_4$, $R_5$, $R_6$, and $R_7$ may each, independently, be selected from hydrogen, trifluoromethyl, nitro, cyano, $C_1$-$C_{20}$ alkyl, an aromatic, a halide, $C_1$-$C_{20}$ alkyl ether, benzyl halide, benzylether, aromatic ether and a combination thereof. In certain embodiments, the optionally substituted triarylphosphite may be triphenylphosphite.

The optionally substituted trialkylphosphite of various embodiments may be of general formula (IV):

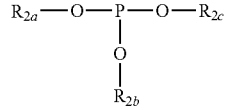

where $R_{2a}$, $R_{2b}$ and $R_{2c}$ may each, independently, be $C_1$-$C_{20}$ alkyls, and in certain embodiments, the optionally substituted trialkylphosphite may be trimethylphosphite.

The optionally substituted alkanol of various embodiments may be selected from optionally substituted alkanols of general formula (V):

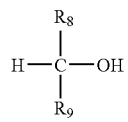

where $R_8$ and $R_9$ may each, independently, be hydrogen or $C_1$-$C_{20}$ alkyl, and in certain embodiments, the optionally substituted alkanol may be methanol.

In some embodiments, the optionally substituted trialkylphosphite or optionally substituted alkanol may be added to the heated catalytic mixture by methods including but not limited to: adding the optionally substituted trialkylphosphite or optionally substituted alkanol under a surface of the heated triarylphosphite catalytic mixture; adding the optionally substituted trialkylphosphite or optionally substituted alkanol on top of a surface of the heated triarylphosphite catalytic mixture; and a combination thereof.

The catalyst of some embodiments may be an alkylating catalyst, and in various embodiments, the catalyst may be an alkyl halide of general formula (VII):

$$R_{10}-X \quad (VII)$$

where $R_{10}$ may be $C_1$-$C_{20}$ alkyl and X may be a halide. In particular embodiments, the catalyst may be $CH_3I$.

In some embodiments, the catalyst is in an excess of less than about 0.15% by weight of a total weight of the optionally substituted trialkylphosphite or optionally substituted alkanol and the optionally substituted triarylphosphite. In other embodiments, the reaction temperature may be at least greater than an exotherm created when an optionally substituted triarylphosphite is mixed at room temperature with a catalyst and an optionally substituted trialkylphosphite and heated, and in particular embodiments, the reaction temperature may be from about 210° C. to about 260° C. In further embodiments, the method may include the step of maintaining the reaction temperature during addition of the mixture.

In certain embodiments, the optionally substituted diaryl alkylphosphonate prepared may include substantially no optionally substituted triarylphosphite, and in certain other embodiments, the optionally substituted diaryl alkylphosphonate prepared may include substantially no optionally substituted arylhalide. Therefore, in particular embodiments, the method may include the step of using the optionally substituted diaryl alkylphosphonate prepared in subsequent reactions without purifying the optionally substituted diaryl alkylphosphonate.

Other embodiments of the invention include a method for preparing an optionally substituted diaryl alkylphosphonate including the steps of providing at least one optionally substituted triarylphosphite; adding to the optionally substituted triarylphosphite at least one catalyst; adding to the optionally substituted triarylphosphite: (i) at least one optionally substituted trialkylphosphite in a molar excess of less than about 10% based on the optionally substituted triarylphosphite; or (ii) at least one optionally substituted alkanol in a molar excess of less than about 10% based on the optionally substituted triarylphosphite; and reacting the optionally substituted triarylphosphite, the at least one catalyst the optionally substituted trialkylphosphite or optionally substituted alkanol to form the optionally substituted diaryl alkylphosphonate.

In some embodiments, the catalyst may be an alkylating catalyst, and in certain embodiments, the catalyst may be an alkyl halide of general formula (VII):

$$R_{10}\text{—}X \qquad (VII)$$

where $R_{10}$ may be $C_1$-$C_{20}$ alkyl and X may be a halide. In particular embodiments, the catalyst may be $CH_3I$. In further embodiments, the catalyst may be in an excess of less than about 0.15% by weight of a total weight of the mixture and the optionally substituted triarylphosphite.

In other embodiments, the step of reacting may include heating to a reaction temperature at least greater than an exotherm created when an optionally substituted triarylphosphite is mixed at room temperature with a catalyst and an optionally substituted trialkylphosphite, and in certain embodiments, the reaction temperature may be from about 210° C. to about 260° C. In still other embodiments, the method may further include the step of maintaining the reaction temperature during the steps of adding and reacting.

Still other embodiments of the invention include a composition including a phosphonium salt prepared by combining: optionally substituted triarylphosphite; and at least one catalyst in an excess of less than about 0.15% of the optionally substituted triarylphosphite.

In some embodiments, the catalyst of the composition may be an alkylating catalyst, and in particular embodiments, the catalyst may be an alkyl halide of general formula (VII):

$$R_{10}\text{—}X \qquad (VII)$$

where $R_{10}$ may be $C_1$-$C_{20}$ alkyl and X may be a halide. In certain embodiments, the catalyst may be $C_3I$.

DETAILED DESCRIPTION

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5% and in still others at most about less than 1%.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, octyl, decyl, tetradecyl, hexadecyl, eicosyl, tetracosyl and the like. "Cycloalkyl" or "cycloalkyl groups" are branched or unbranched hydrocarbons in which all or some of the carbons are arranged in a ring such as but not limited to cyclopentyl, cyclohexyl, methylcyclohexyl and the like. The term "lower alkyl" includes an alkyl group of 1 to 10 carbon atoms.

The term "aryl" or "aryl group" refers to monovalent aromatic hydrocarbon radicals or groups consisting of one or more fused rings in which at least one ring is aromatic in nature. Aryls may include but are not limited to phenyl, napthyl, biphenyl ring systems and the like. The aryl group may be unsubstituted or substituted with a variety of substituents including but not limited to alkyl, alkenyl, halide, benzylic, alkyl or aromatic ether, nitro, cyano and the like and combinations thereof.

"Substituent" refers to a molecular group that replaces a hydrogen in a compound and may include but are not limited to trifluoromethyl, nitro, cyano, $C_1$-$C_{20}$ alkyl, aromatic or aryl, halide (F, Cl, Br, I), $C_1$-$C_{20}$ alkyl ether, benzyl halide, benzyl ether, aromatic or aryl ether, hydroxy, alkoxy, amino, alkylamino (—NHR'), dialkylamino (—NR'R") or other groups which do not interfere with the formation of the diaryl alkylphosphonate.

As defined herein, an "arylol" or an "arylol group" is an aryl group with a hydroxyl, OH, group substituent on the aryl ring. Non-limiting examples of an arylol are phenol, naphthalene and the like. A wide variety of arylols may be used in the embodiments of the invention and are commercially available.

The term "alkanol" or "alkanol group" refers to a compound including an alkyl of 1 to 20 carbon atoms or more having at least one hydroxyl group substituent. Examples of alkanols include but are not limited to methanol, ethanol, 1- and 2-propanol, 1,1-dimethylethanol, hexanol, octanol and the like. Alkanol groups may be optionally substituted with substituents as described above.

The term "alkenol" or "alkenol group" refers to a compound including an alkene 2 to 20 carbon atoms or more having at least one hydroxyl group substituent. The hydroxyl may be arranged in either isomeric configuration (cis or trans). Alkenols may be further substituted with one or more substituents as described above and may be used in place of alkanols in some embodiments of the invention. Alkenols are known to those skilled in the art and many are readily available commercially.

Embodiments of the invention presented herein include methods for making optionally substituted diaryl alkylphosphonates, optionally substituted diaryl alkylphosphonates prepared using such methods, and compositions related to these methods. The method of various embodiments may include combining optionally substituted triarylphosphite with an at least less than 10% molar excess of either optionally substituted trialkylphosphite or optionally substituted alkanol and a catalytically effective amount of a catalyst. In embodiments, the optionally substituted triarylphosphite may be heated to a defined reaction temperature prior to the addition of the optionally substituted trialkylphosphite or optionally substituted alkanol and a catalytically effective amount of a catalyst, and this reaction mixture may be reacted to form optionally substituted diaryl alkylphosphonate. Without wishing to be bound by theory, combining the components at ambient temperature and heating to a suitable reaction temperature may induce an uncontrolled exothermic reaction to occur potentially creating a violent exotherm.

In certain embodiments, optionally substituted diaryl alkylphosphonate may form immediately upon addition of the optionally substituted trialkylphosphite or optionally substituted alkanol and a catalytically effective amount of the catalyst to the heated optionally substituted triarylphosphite. In other embodiments, the heat generated by the reaction may be regulated by the rate at which the optionally substituted trialkylphosphite or optionally substituted alkanol and a catalytically effective amount of the catalyst are added to the heated optionally substituted triarylphosphite. Therefore, the optionally substituted trialkylphosphite or optionally substituted alkanol and a catalytically effective amount of the catalyst may be added using a controlled method such as, for example, dropping in from above or pumping in from below the surface of the reaction mixture.

In still other embodiments, optionally substituted triarylphosphite and a catalytically effective amount of a catalyst, such as, but not limited to, a methyl halide may be combined to form a stable triarylphosphite catalytic mixture. The triarylphosphite catalytic mixture may be stored following its preparation at ambient temperature for an indefinite period of time, and/or the triarlyphosphite catalytic mixture may be heated to a defined reaction temperature and production of optionally substituted diaryl alkylphosphonate may be initiated by the addition of an at least less than 10% molar excess of optionally substituted trialkylphosphite or optionally substituted alkanol to the heated triarylphosphite catalytic mixture. The triarylphosphite catalytic mixture of embodiments may further contain an excess of optionally substituted triarylphosphite in relation to the catalyst.

Without wishing to be bound by theory, when combined with the catalyst, the optionally substituted triarylphosphite may react with the catalyst to form the triarylphosphite catalytic mixture such which substantially no uncontrolled exothermic reaction is observed. In some embodiments, the rate of addition of trialkylphosphite to heated reaction mixture may be adjusted to additionally control the exotherm. Moreover, the triarlyphosphite catalytic mixture may substantially increase the boiling point of the catalyst such that the triarylphosphite catalytic mixture may be heated to a temperature greater than 40° C. with substantially no loss of catalytic activity. Therefore, production of optionally substituted diaryl alkylphosphonate may take place at high temperature with substantially no loss of the catalyst due to vaporization of the catalyst as may occur when the catalyst is added with the optionally substituted trialkylphosphite or optionally substituted alkanol or added individually either by dropping into the reaction or pumping in from below the reaction surface.

In certain embodiments, optionally substituted diaryl alkylphosphonate may form immediately upon addition of the optionally substituted trialkylphosphite or optionally substituted alkanol to the heated triarylphosphite catalytic mixture. In other embodiments, the heat generated by the reaction may be regulated by the rate at which the optionally substituted trialkylphosphite or optionally substituted alkanol are added to the heated triarylphosphite catalytic mixture. Therefore, the optionally substituted trialkylphosphite or optionally substituted alkanol may he added using a controlled method such as, for example, dropping in from above or pumping in from below the surface of the reaction mixture.

In embodiments of the invention, the defined reaction temperature may be at least higher than the highest exotherm when the components are mixed at ambient temperature and heated allowing the reaction to occur, and in certain embodiments, the reaction temperature may be at least greater than the temperature of the highest exotherm and below the temperature at which the optionally substituted diaryl alkylphosphonate produced is thermally degraded. The reaction temperature of embodiments may therefore be from about 210° C. to about 260° C., and in others, the reaction temperature may be from about 230° C. to about 260° C. Without wishing to be bound by theory, the large observed uncontrolled exotherm, when the reactants are combined at room temperature and heated, may be eliminated by performing the reaction at a temperature at least greater than the highest exotherm and the volatility of the reaction mixture may be reduced allowing for the reaction to occur more safely.

The optionally substituted diaryl alkylphosphonates prepared by any of the methods described above may be substantially free of contaminants, such as, for example residual optionally substituted triarylphosphite which may allow optionally substituted diaryl alkylphosphonates prepared using methods of embodiments of the invention to be used in subsequent condensation reactions with substantially no formation of toxic by-products.

The diaryl alkylphosphonates or optionally substituted diaryl alkylphosphonates of embodiments may be of general formula (I):

(I)

where $R_2$ may be $C_1$-$C_{20}$ alkyl and $R_1$ may be an aromatic or aryl group, or a substituted aryl group of formula (II):

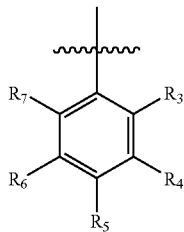

(II)

where $R_3$, $R_4$, $R_5$, $R_6$, and $R_7$ may independently be any substituent including but not limited to hydrogen, $C_1$-$C_{20}$ alkyl, aromatic or aryl group, trifluoromethyl, nitro, cyano, halide (F, Cl, Br, I), $C_1$-$C_{20}$ alkyl ether, benzyl halide, benzyl ether, aromatic or aryl ether, or optionally substituted versions of these, and $R_3$, $R_4$, $R_5$, $R_6$, and $R_7$ are essentially unaffected by the reaction. In certain embodiments, the diaryl alkylphosphonate may be diphenyl methylphosphonate.

Optionally substituted triarylphosphite may be of general formula (III).

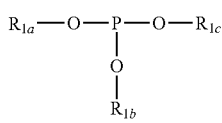

(III)

where $R_{1a}$, $R_{1b}$ and $R_{1c}$ may, individually, be an aromatic or aryl group, or a substituted aryl group of formula (II), and in some embodiments, the triarylphosphite may be triphenylphosphite.

Optionally substituted trialkylphosphites may be of general formula (IV):

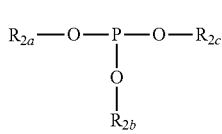

(IV)

where $R_{2a}$, $R_{2b}$ and $R_{2c}$ may, individually, be $C_1$-$C_{20}$ alkyl, and in some embodiments, the trialkylphosphite may be trimethylphosphite.

Optionally substituted alkanols of embodiments presented herein, may be of general formula (V).

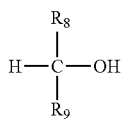

(V)

where $R_8$ and $R_9$ may independently be hydrogen or $C_1$-$C_{20}$ alkyl, and in some embodiments, the optionally substituted alkanol may be methanol.

Various molar ratios of the reactants may be used in embodiments of the invention. In some embodiments, the optionally substituted trialkylphosphite or optionally substituted alkanol may be provided in a molar excess relative to the optionally substituted triarylphosphite that is at least less than about 10%. In other embodiments, the optionally substituted trialkylphosphite or optionally substituted alkanol may be in molar excess of at least less than about 9.5%, 9.0% or 8.0% relative to the optionally substituted triarylphosphite, and in still other embodiments, the optionally substituted trialkylphosphite or optionally substituted alkanol may be in a molar excess of from about 0.0% to about 10% molar excess relative to the optionally substituted triarylphosphite or from about 0.01% to about 3.0% molar excess relative to the optionally substituted triarylphosphite. In certain embodiments, the optionally substituted trialkylphosphite or optionally substituted alkanol may be provided in a molar excess of less than 1% relative to the optionally substituted triarylphosphite. Without wishing to be bound by theory, when the optionally substituted trialkylphosphite or optionally substituted alkanol is provided within the range of 0.0% and about 3.0% relative to the optionally substituted triarylphosphite formation of by-products such as, for example, dimethylphenyl phosphite can be avoided.

In embodiments in which the optionally substituted alkanol or optionally substituted trialkylphosphite are provided in molar excess relative to the optionally substituted triarylphosphite, the diaryl alkylphosphonate produced may contain substantially no contaminants such as, for example, residual triarylphosphite, residual trialkylphosphite or combination thereof. Residual triarylphosphite may be difficult to purify from diaryl alkylphosphonate because the boiling points of the two compounds are similar, and triarylphosphite may not be distilled away from diaryl alkylphosphonate. Moreover, even a small amount, for example, less than 1% of the total product, of residual triarylphosphite may react with conjugated bisphenols and may be reduced to form toxic phosphines. Additionally, oxidized bisphenol may form colored by-products. In any case, the resulting oligomeric or polyphosphonate may be tainted and useable or extensive distillation may be required to remove by-products or residual reactants from the diaryl alkylphosphonate product which greatly increases the time and cost required to produce a usable product.

In some embodiments, the catalyst may include, but are not limited to, alkyl chlorides, alkyl bromides and alkyl iodides in which the alkyl groups may carry one or more of a variety of substituents. In other embodiments, methyl iodide may be the catalyst. Other known alkylating catalysts that may be used in the present invention include, but are not limited to, sulfonic acid esters, sulfuric acid esters, and sulfones. Strong acids such as, but not limited to, trifluoromethane sulfonic acid, perfluorobutane sulfonic acid and perfluorooctane sulfonic acid may also serve as catalysts in this reaction. The amount of catalyst added to the reaction may vary among embodiments. However, in some embodiments, the catalyst may be in excess of from about 0.01% to about 10% by weight relative to the total weight of the optionally substituted triarylphosphite and the optionally substituted trialkylphosphite or optionally substituted alkanol. In particular embodiments, the catalyst may be less than about 0.15% by weight relative to the total weight of the optionally substituted triarylphosphite and the optionally substituted trialkylphosphite or optionally substituted alkanol. Without wishing to be bound by theory, when the catalyst is less than about 0.15% by weight of the total reactants, the formation of by-products such as, for example, iodobenzene and triphenylphosphate may be avoided.

While the optionally substituted trialkylphosphite or optionally substituted alkanol and the catalyst may individually be provided in the ranges described herein above, in certain embodiments, the optionally substituted trialkylphosphite or optionally substituted alkanol and the catalyst may both be provided in the range described above. For example, in one embodiment, the optionally substituted trialkylphosphite or optionally substituted alkanol may be in molar excess of less than 10% by weight of the optionally substituted triarylphosphite and the catalyst may be less than 0.15% by weight relative to the total weight of the optionally substituted triarylphosphite and the optionally substituted trialkylphosphite or optionally substituted alkanol. In another embodiment, the optionally substituted trialkylphosphite or optionally substituted alkanol may be in molar excess of about 0.01% to about 3% by weight relative to the optionally substituted triarylphosphite or less than 1% by weight relative to the optionally substituted triarylphosphite and the catalyst may be less than 0.15% by weight relative to the total weight of the optionally substituted tnrarylphosphite and the optionally substituted trialkylphosphite or optionally substituted alkanol.

The method of the present invention is not limited by how a catalyst is added. For example, the catalyst may be combined with the optionally substituted triarylphosphite prior to the addition of the optionally substituted alkanol or optionally substituted alkylphosphite, or the catalyst may be added concurrently with the addition of optionally substituted alkanol or optionally substituted alkylphosphite.

In embodiments, one or more reactant and/or catalysts may be added from above onto the upper surface of the reaction mixture. For example, optionally substituted trialkylphosphite, or optionally substituted alkanol and a catalyst, may be added to a reaction mixture containing optionally substituted triarylphosphite or triarylphosphite and a catalyst via an addition funnel. The alkanol or alkanol and catalyst mixture may then be dropped onto the surface of the reaction mixture in a controlled manner. In other embodiments, the optionally substituted alkanol, or optionally substituted alkanol and a catalyst, may be pumped into the reaction mixture thereby adding the alkanol or alkanol and catalyst mixture from below the surface of the reaction mixture. Pumping components into a reaction mixture may allow for a constant stream of optionally substituted trialkylphosphite or optionally substituted alkanol and a catalyst to be provided to heated optionally substituted triarylphosphite. Or, optionally substituted alkanol may be provided to heated triarylphosphite catalytic mixture from below the surface of the reaction mixture in a controlled manner. Without wishing to be bound by theory, adding components such as the optionally substituted alkanol, optionally substituted trialkylphosphite, and or a catalyst from below the surface of the reaction mixture may allow for improved residence time of that component in the reaction mixture increasing the time in which the reactants may react since the heat evolved during the reaction or the defined reaction temperature may be such that one or more of these components evaporate out of the reaction mixture if added to the surface of the reaction mixture. Adding the reaction components from below may result in improved reaction efficiency, conversion time, and product yield. In other embodiments, the feed rate of the optionally substituted trialkylphoshite or optionally substituted alkanol and a catalyst may be increased by pumping these components beneath the surface of the reaction mixture reducing the reaction time compared to the overhead addition method by as much as by half.

Without wishing to be bound by theory in embodiments in which triarylphosphite is reacted with trialkyl phosphite, the synthesis of diaryl alkylphosphonate may occur, for example, as illustrated in scheme (I):

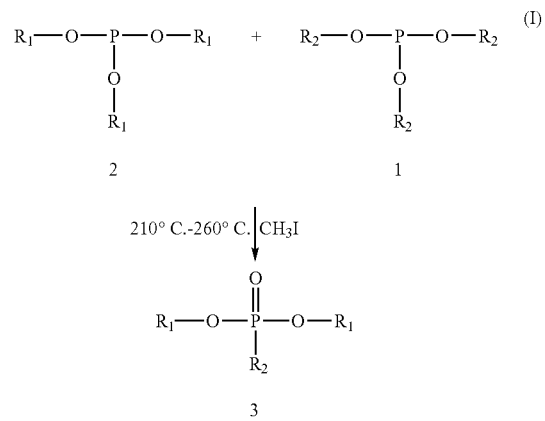

wherein $R_1$ may be an aromatic or aryl group, or a substituted aryl group of formula (II) and $R_2$ may be $C_1$-$C_{20}$ alkyl.

In embodiments in which triarylphosphite is reacted with optionally substituted alkanol, the synthesis of diaryl alkylphosphonate may occur, for example, as illustrated in scheme (II):

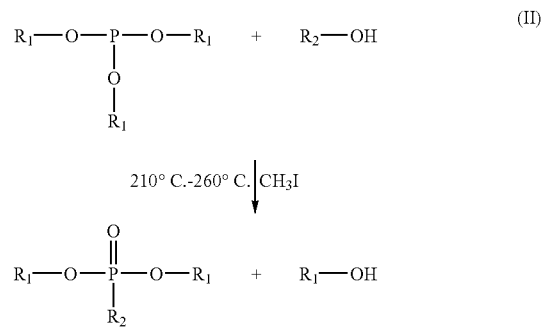

wherein $R_1$ may be an aromatic or aryl group, or a substituted aryl group of formula (II) and $R_2$ may be $C_1$-$C_{20}$ alkyl.

Still other embodiments, a triarylphosphite catalytic mixture, may be formed by combining optionally substituted triarylphosphite with a catalyst such as, for example, a methyl halide catalyst, and heated to a defined reaction temperature before the addition of optionally substituted trialkylphosphite or optionally substituted alkanol resulting in a catalyst of general formula (VI):

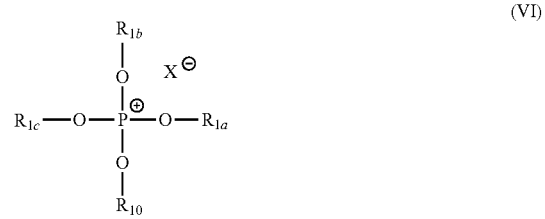

wherein $R_{1a}$, $R_{1b}$ and $R_{1c}$ may be an aromatic or aryl group, or a substituted aryl group of formula (II); $R_{10}$ may be hydrogen or $C_1$-$C_{20}$ alkyl; and X may be a halide such as F, Cl, Br, or I. The catalyst of such embodiments may be stable at ambient temperature, or heated to a temperature up to about 260° C. without loss of catalytic activity. The stability of the catalytic complex may be such that the catalyst complex may be stored for an indefinite period of time. The reaction by which the catalyst of embodiments is formed may be reversed at high temperature. Therefore in some embodiments, the catalyst of general formula VI and optionally substituted triarylphosphite may be heated to a defined reaction temperature of at least about 210° C. and optionally substituted alkanol or optionally substituted trialkylphosphite may be added to create a reaction mixture used to prepare optionally substituted diaryl alkylphosphonate. In such embodiments, diaryl alkylphosphonate may be prepared without providing an additional catalyst.

Advantageously, the diaryl alkylphosphonates produced by embodiments of the invention may be prepared in one-pot, so there may be no need to isolate or purify intermediates. Additionally, by-products such as dialkyl arylphosphite, triarylphosphite, arylols, methoxyaryls, diaryl alkylphosphates, diaryl methylphosphite and residual triarylphosphite may be minimized or eliminated, so one or more separation steps in which by-products are removed may not be necessary. In certain embodiments, triarylphosphate may be avoided as a by-product. The diaryl alkyphosphonates produced by the present invention may, therefore, be easier to purify or produce at a level of purity sufficient for subsequent reactions.

A wide variety of diaromatic alkylphosphonates may be produced using the present invention. These may be used as monomers in the synthesis of polymers, such as, but not limited to, polyphosphonates and copolymers of carbonates and phosphonates. These polymers have exceptional fire resistance and are useful in a wide variety of applications encountered in everyday life.

Having generally described the invention, a more complete understanding thereof may be obtained by reference to the following examples that are provided for purposes of illustration only and do not limit the invention.

EXAMPLE 1

7.0% Excess Trimethylphophite and 1 wt % Iodoniethane. A 5 liter flask equipped with an overhead stirrer, oil bath, addition funnel, water-cooled condenser with nitrogen by-pass, and thermometer was used as the reaction vessel. The flask was charged with 2560 grams (8.0 moles) of triphenylphosphite and 36.8 grams (0.256 moles, 1 wt % of total reactants) of iodomethane, and these components were mixed at room temperature. This mixture was then heated under $N_2$ to a reaction temperature 240° C. During heating, no exotherm or refluxing is observed. Some discoloration occurred during heating, but this disappeared after addition of trimethylphosphite. When the reaction temperature was reached solution of 550 grams (4.3 moles, 7.0% molar excess) of trimethylphosphite was added from a feeding funnel over 3 hours. After addition, the reaction temperature of 240° C. was maintained for an additional hour. The product was than cooled to room temperature and analyzed.

The crude products were analyzed by gas chromatography. Pure standards of each starting material and the product were used to establish retention times. From this analysis, the amount of the desired product, residual starting materials, and any side products were measured. The crude reaction mixture was diluted with acetone and injected into the gas chromatograph. All of the peaks measured were assigned a chemical structure. Analysis of the mixture by gas chromatography gave the following results:

Dimethyl phenylphosphite (DMPP(i))=3.25%
Diphenyl methylphosphonate (DPP)=94.70%
Triphenylphosphate (TPP (a))=2.05%
Phenol=0.0%
Iodobenzene=0.0%.

EXAMPLE 2-4

0.80% Excess Trimethylphosphite and 0.15 wt % Iodomethane. In each of examples 2-4, a 12 liter flask equipped with an overhead stirrer, oil bath, addition funnel, water-cooled condenser with nitrogen by-pass, and thermometer was used as the reaction vessel. The flask was charged with 6773 grams (21.17 moles) of triphenylphosphite and 12 grams (0.084 moles, 0.15 wt % of total reactants) of iodomethane, and these components were mixed at room temperature. This mixture was then heated under $N_2$ to a reaction temperature 240° C. During heating, no exotherm or refluxing is observed. Some discoloration occurred during heating, but this disappeared after addition of trimethylphosphite. When the reaction temperature was reached solution of 1365 grams (10.67 moles, 0.80% molar excess) of trimethylphosphite was added from a feeding funnel over 3-3.5 hours. No refluxing was observed during feeding of trimethylphosphite. After addition, the reaction temperature of 240° C. to 260° C. was maintained following the reaction. The reaction was terminated after gas chromatography was performed on the reaction mixture showing that not traces of the starting could be detected. Results of analysis of the mixture by gas chromatography are reported in Table 1. Table 1 shows the product (diphenyl methylphosphonate (DPP)) and by-products of the reaction (triphenylphosphate (TPP(a)), phenol and iodobenzene).

| Example No. | DPP % | TPP(a) % | Phenol % | Iodobenzene % |
| --- | --- | --- | --- | --- |
| 2 | 99.4 | 0.6 | 0.0 | 0.0 |
| 3 | 99.1 | 0.9 | 0.0 | 0.0 |
| 4 | 98.7 | 0.0 | 1.3 | 0.0 |

EXAMPLE 5-7

1.17% Excess Trimethylphosphite and 0.10 wt % Iodomethane. In each of examples 5-7, a 12 liter flask equipped with an overhead stirrer, oil bath, addition funnel, water-cooled condenser with nitrogen by-pass, and thermometer was used as the reaction vessel. The flask was charged with 6773 grams (21.17 moles) of triphenylphosphite and 8.0 grams (0.056 moles, 0.10 wt % of total reactants) of iodomethane, and these components were mixed at room temperature. This mixture was then heated under $N_2$ to a reaction temperature 240° C. During heating, no exotherm or refluxing is observed. Some discoloration occurred during heating, but this disappeared after addition of trimethylphosphite. When the reaction temperature was reached, a solution of 1370 grams (10.71 moles, 1.17% molar excess) of trimethylphosphite was added from a feeding funnel over 3-3.5 hours. No refluxing was observed during feeding of trimethylphosphite. After addition, the reaction temperature of 240° C. to 260° C. was maintained following the reaction. The reaction was terminated after gas chromatography was performed on the reaction mixture showing that not traces of the starting could be detected. Results of analysis of the mixture by gas chromatography are reported in Table 2. Table 2 shows the product (diphenyl methylphosphonate (DPP)) and by-products of the reaction (triphenylphosphate (TPP(a)), phenol and iodobenzene).

| Example No. | DPP % | TPP(a) % | Phenol % | Iodobenzene % |
|---|---|---|---|---|
| 5 | 99.5 | 0.0 | 0.5 | 0.0 |
| 6 | 99.5 | 0.0 | 0.5 | 0.0 |
| 7 | 98.4 | 0.0 | 1.6 | 0.0 |

EXAMPLE 8-10

1.25% Excess Trimethylphosphite and 0.074 wt % Iodomethane. In each of examples 8-10, a 12 liter flask equipped with an overhead stirrer, oil bath, addition funnel, water-cooled condenser with nitrogen by-pass, and thermometer was used as the reaction vessel. The flask was charged with 6773 grams (21.17 moles) of triphenylphosphite and 6.0 grams (0.042 moles, 0.074 wt % of total reactants) of iodomethane, and these components were mixed at room temperature. This mixture was then heated under $N_2$ to a reaction temperature 240° C. During heating, no exotherm or refluxing is observed. Some discoloration occurred during heating, but this disappeared after addition of trimethylphosphite. When the reaction temperature was reached, a solution of 1372 grams (10.72 moles, 1.25% molar excess) of trimethylphosphite was added from a feeding funnel over 3-3.5 hours. No refluxing was observed during feeding of trimethylphosphite. After addition, the reaction temperature of 240° C. to 260° C. was maintained following the reaction. The reaction was terminated after gas chromatography was performed on the reaction mixture showing that not traces of the starting could be detected. Results of analysis of the mixture by gas chromatography are reported in Table 3. Table 3 shows the product (diphenyl methylphosphonate (DPP)) and by-products of the reaction (triphenylphosphate (TPP(a)), phenol and iodobenzene).

| Example No. | DPP % | TPP(a) % | Phenol % | Iodobenzene % |
|---|---|---|---|---|
| 8 | 99.3 | 0.0 | 0.7 | 0.0 |
| 9 | 100 | 0.0 | 0.0 | 0.0 |
| 10 | 99.4 | 0.0 | 0.6 | 0.0 |

EXAMPLE 11

0.80% Excess Trimethylphosphite and 0.074 wt % Iodomethane. A 12 liter flask equipped with an overhead stirrer, oil bath, addition funnel, water-cooled condenser with nitrogen by-pass, and thermometer was used as the reaction vessel. The flask was charged with 6773 grams (21.17 moles) of triphenylphosphite and 6.0 grams (0.042 moles, 0.074 wt % of total reactants) of iodomethane, and these components were mixed at room temperature. This mixture was then heated under $N_2$ to a reaction temperature 240° C. During heating, no exotherm or refluxing is observed. Some discoloration occurred during heating, but this disappeared after addition of trimethylphosphite. When the reaction temperature was reached, a solution of 1365 grams (10.67 moles, 0.80% molar excess) of trimethylphosphite was added from a feeding funnel over 3-3.5 hours. No refluxing was observed during feeding of trimethylphosphite. After addition, the reaction temperature of 240° C. to 260° C. was maintained following the reaction. The reaction was terminated after gas chromatography was performed on the reaction mixture showing that not traces of the starting could be detected. Results of analysis of the mixture by gas chromatography are as follows:

Diphenyl methylphosphonate (DPP)=98.65%
Triphenylphosphate (TPP(a))=0.0%
Phenol=1.35%
Iodobenzene=0.0%

What is claimed is:

1. A method for preparing optionally substituted diaryl alkylphosphonate comprising:
   combining at least one optionally substituted triarylphosphite and at least one catalyst to form a triarylphosphite catalytic mixture;
   heating the triarylphosphite catalytic mixture to a reaction temperature of from 210° C. to 260° C.;
   adding to the heated triarylphosphite catalytic mixture at least one optionally substituted trialkylphosphite in a molar excess of less than 10% based on the optionally substituted triarylphosphite; and
   reacting the triarylphosphite mixture and the at least one optionally substituted trialkylphosphite to form the optionally substituted diaryl alkylphosphonate.

2. The method of claim 1, wherein the optionally substituted trialkylphosphite is in a molar excess of 0.0% to 3% of the optionally substituted triarylphosphite.

3. The method of claim 1, wherein the optionally substituted trialkylphosphite is in a molar excess of less than 1% of the optionally substituted triarylphosphite.

4. The method of claim 1, wherein the optionally substituted triarylphosphite is of general formula (III):

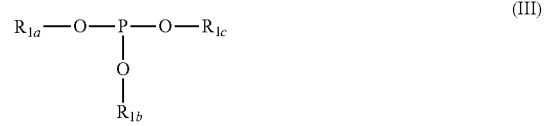

(III)

wherein $R_{1a}$, $R_{1b}$ and $R_{1c}$ are each, independently, of general formula (II):

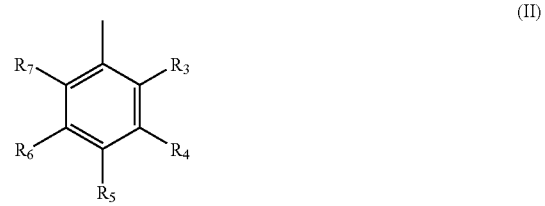

(II)

wherein $R_3$, $R_4$, $R_5$, $R_6$, and $R_7$ are each, independently, selected from hydrogen, trifluoromethyl, nitro, cyano, $C_1$-$C_{20}$ alkyl, an aromatic, a halide, $C_1$-$C_{20}$ alkyl ether, benzyl halide, benzylether, aromatic ether and a combination thereof.

5. The method of claim 1, wherein the optionally substituted triarylphosphite is triphenylphosphite.

6. The method of claim 1, wherein the optionally substituted trialkylphosphite is of general formula (IV):

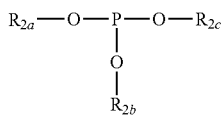

(IV)

wherein $R_{2a}$, $R_{2b}$ and $R_{2c}$ are each, independently, $C_1$-$C_{20}$ alkyls.

7. The method of claim 1, wherein the optionally substituted trialkylphosphite is trimethylphosphite.

8. The method of claim 1, wherein the catalyst is an alkylating catalyst.

9. The method of claim 1, wherein the catalyst is an alkyl halide of general formula (VII):

$R_{10}$—X  (VII)

wherein $R_{10}$ is $C_1$-$C_{20}$ alkyl; and
X is a halide.

10. The method of claim 1, wherein the catalyst is $CH_3I$.

11. The method of claim 1, wherein the catalyst is in an excess of less than 0.15% by weight of a total weight of the optionally substituted trialkylphosphite and the optionally substituted triarylphosphite.

12. The method of claim 1, wherein the reaction temperature is at least greater than an exotherm created when an optionally substituted triarylphosphite is mixed at room temperature with a catalyst and an optionally substituted trialkylphosphite and heated.

13. The method of claim 1, further comprising maintaining the reaction temperature during addition of the mixture.

14. The method of claim 1, wherein the optionally substituted diaryl alkylphosphonate prepared comprises substantially no optionally substituted triarylphosphite.

15. The method of claim 1, wherein the optionally substituted diaryl alkylphosphonate prepared comprises substantially no optionally substituted arylhalide.

16. The method of claim 1, further comprising using the optionally substituted diaryl alkylphosphonate prepared in subsequent reactions without purifying the optionally substituted diaryl alkylphosphonate.

17. The method of claim 1, wherein the triarylphosphite catalytic mixture is stored for an indefinite period of time prior to heating.

18. A method for preparing an optionally substituted diaryl alkylphosphonate comprising:
heating at least one optionally substituted triarylphosphite to a reaction temperature of from 210° C. to 260° C.;
adding to the optionally substituted triarylphosphite at least one catalyst;
adding to the optionally substituted triarylphosphite at least one optionally substituted trialkylphosphite in a molar excess of less than 10% based on the optionally substituted triarylphosphite; and
reacting the optionally substituted triarylphosphite, the at least one catalyst, and the optionally substituted trialkylphosphite to form the optionally substituted diaryl alkylphosphonate.

19. The method of claim 18, wherein the catalyst is an alkylating catalyst.

20. The method of claim 18, wherein the catalyst is an alkyl halide of general formula (VII):

$R_{10}$—X  (VII)

wherein $R_{10}$ is $C_1$-$C_{20}$ alkyl; and
X is a halide.

21. The method of claim 18, wherein the catalyst is $CH_3I$.

22. The method of claim 18, wherein the catalyst is in an excess of less than 0.15% by weight of a total weight of the mixture and the optionally substituted triarylphosphite.

23. The method of claim 18, wherein the reaction temperature is at least greater than an exotherm created when an optionally substituted triarylphosphite is mixed at room temperature with a catalyst and an optionally substituted trialkylphosphite and heated.

24. The method of claim 18, further comprising maintaining the reaction temperature during the steps of adding and reacting.

* * * * *